United States Patent [19]
Beaupre

[11] Patent Number: 5,938,633
[45] Date of Patent: Aug. 17, 1999

[54] ULTRASONIC SURGICAL DEVICES

[75] Inventor: Jean Beaupre, Cincinnati, Ohio

[73] Assignee: Ethicon Endo-Surgery, Inc., Cincinnati, Ohio

[21] Appl. No.: 08/890,262

[22] Filed: Jul. 9, 1997

[51] Int. Cl.$^6$ .................................................. A61B 17/20
[52] U.S. Cl. ............................................................ 604/22
[58] Field of Search .............................. 604/22, 53, 114; 606/169, 167, 171, 178

[56] References Cited

U.S. PATENT DOCUMENTS

| | | | |
|---|---|---|---|
| Re. 30,536 | 3/1981 | Perdreaux, Jr. | 433/86 |
| 2,874,470 | 2/1959 | Richards | 32/58 |

(List continued on next page.)

FOREIGN PATENT DOCUMENTS

| | | |
|---|---|---|
| 1098003 | 9/1977 | Canada . |
| 0 624 346 A2 | 5/1994 | European Pat. Off. . |
| 0 624 346 A3 | 5/1994 | European Pat. Off. . |
| 29 22 239 | 5/1979 | Germany . |
| 37 07 921 A1 | 3/1987 | Germany . |
| 56-108085 | of 1981 | Japan . |
| 56-38931 | of 1981 | Japan . |
| 61-265136 | of 1986 | Japan . |
| 2-99049 | of 1990 | Japan . |
| 1388002 A1 | 4/1988 | U.S.S.R. . |
| WO 91/13591 | 3/1991 | WIPO . |
| WO 93/16646 | 1/1993 | WIPO . |
| WO 96/29935 | 4/1996 | WIPO . |
| WO 96/34561 | 5/1996 | WIPO . |
| WO 97/07735 | 8/1996 | WIPO . |

OTHER PUBLICATIONS

Mike Fillon, "A Kinder Cut", Popular Mechanics, 90–91, (Oct. 1996).

"PLC's Heart Laser Takes Over Center Stage", In Vivo, The Business and Medicine Report, 9–14, (Apr. 1995).

H.T. Aretz, "Intraluminal Ultrasound Guidance of Transverse Laser Coronary Atherectomy", SPIE vol. 1201, Optical Fibers In Medicine V, 68–78, (1990).

Hardy et al., "Regional Myocardial Blood Flow and Cardian Mechanics In Dog Hearts With $CO_2$ Laser–Induced Intramyocardial Revascularization", Basics Res. Cardiol., vol. 85, No. 2, pp. 179–196.

Jeevanandam et al., "Myocardial Revascularization By Laser–Induced Channels", Surgical Forum XLI, 225–227 (Oct. 1990).

Mirhoseini et al., "Clinical and Histological Evaluation of Laser Myocardial Revascularization", Journal of Clinical Laser Medicine & Surgery, 73–78 (Jun. 1990).

Mirhoseini et al., "New Concepts In Revascularization of the Myocardium", Ann. Thorac. Surg., 45:415–420 (Apr. 1988).

Mirhoseini et al., "Laser Myocardial Revascularization, Lasers in Surgery and Medicine", 459–461 (1986).

Mirhoseini, Medical Instrumentation, vol. 17, No. 6, 397–403 (Nov. –Dec. 1983).

(List continued on next page.)

*Primary Examiner*—Manuel Mendez

[57] ABSTRACT

The present invention relates to surgical devices. A surgical instrument in accordance with the present invention includes a transducer assembly adapted to vibrate at an ultrasonic frequency. An end effector is adapted to receive ultrasonic vibration from the transducer assembly and to propagate the ultrasonic vibration from a first end to a second end. The end effector is rotatable with respect to the handpiece assembly while the transducer assembly vibrates at the ultrasonic frequency. A method of applying ultrasonic energy to tissue of a patient is also provided. The method includes the steps of providing a handpiece assembly carrying an acoustic assembly having a transducer assembly and an end effector, and energizing the transducer to cause the end effector to vibrate. The method further includes the steps of rotating the end effector with respect to the handpiece assembly while the transducer assembly is vibrating, and contacting the tissue of the patient with the end effector.

25 Claims, 5 Drawing Sheets

U.S. PATENT DOCUMENTS

| | | | |
|---|---|---|---|
| 3,075,288 | 1/1963 | Balamuth et al. | 32/58 |
| 3,076,904 | 2/1963 | Kleesattel et al. | 310/26 |
| 3,213,537 | 10/1965 | Balamuth et al. | 32/28 |
| 3,352,303 | 11/1967 | Delaney | 128/24 |
| 3,368,280 | 2/1968 | Fridman et al. | 32/58 |
| 3,375,583 | 4/1968 | Blank et al. | 32/26 |
| 3,488,851 | 1/1970 | Haydu | 32/58 |
| 3,489,930 | 1/1970 | Shoh | 310/8.1 |
| 3,518,766 | 7/1970 | Burt | 32/58 |
| 3,526,036 | 9/1970 | Goof | 32/28 |
| 3,526,792 | 9/1970 | Shoh | 310/8.1 |
| 3,589,012 | 6/1971 | Richman | 32/58 |
| 3,589,363 | 6/1971 | Banko et al. | 128/276 |
| 3,593,425 | 7/1971 | Robinson | 32/58 |
| 3,636,947 | 1/1972 | Balamuth | 128/66 |
| 3,654,502 | 4/1972 | Carmona et al. | 310/26 |
| 4,658,817 | 4/1987 | Hardy | 128/303.1 |
| 4,676,231 | 6/1987 | Hisazumi et al. | 128/6 |
| 4,693,556 | 9/1987 | McCaughan, Jr. | 350/320 |
| 4,816,018 | 3/1989 | Parisi | 604/22 |
| 4,820,152 | 4/1989 | Warrin et al. | 433/86 |
| 4,867,141 | 9/1989 | Nakada et al. | 128/24 |
| 4,870,953 | 10/1989 | DonMichael et al. | 128/24 |
| 4,890,898 | 1/1990 | Bentley et al. | 350/96.23 |
| 4,897,079 | 1/1990 | Zaleski et al. | 604/22 |
| 4,920,954 | 5/1990 | Alliger et al. | 128/24 |
| 4,922,902 | 5/1990 | Wuchinich et al. | 604/22 |
| 4,931,047 | 6/1990 | Broadwin et al. | 604/22 |
| 4,936,281 | 6/1990 | Stasz | 128/660.03 |
| 4,974,162 | 11/1990 | Siegel et al. | 364/413.06 |
| 4,974,590 | 12/1990 | Saito | 128/662.06 |
| 4,979,952 | 12/1990 | Kubota et al. | 606/169 |
| 4,997,431 | 3/1991 | Isner et al. | 606/15 |
| 5,011,471 | 4/1991 | Miyazaki et al. | 604/22 |
| 5,026,387 | 6/1991 | Thomas | 606/169 |
| 5,047,043 | 9/1991 | Kubota et al. | 606/169 |
| 5,057,119 | 10/1991 | Clark et al. | 606/169 |
| 5,059,210 | 10/1991 | Clark et al. | 606/169 |
| 5,069,664 | 12/1991 | Guess et al. | 604/22 |
| 5,091,404 | 2/1992 | Elgebaly | 514/401 |
| 5,106,386 | 4/1992 | Isner et al. | 606/15 |
| 5,112,300 | 5/1992 | Ureche | 604/22 |
| 5,123,903 | 6/1992 | Quaid et al. | 604/22 |
| 5,125,924 | 6/1992 | Rudko | 606/12 |
| 5,125,926 | 6/1992 | Rudko et al. | 606/19 |
| 5,151,084 | 9/1992 | Khek | 604/22 |
| 5,151,085 | 9/1992 | Sakurai et al. | 604/22 |
| 5,160,317 | 11/1992 | Costin | 604/22 |
| 5,167,725 | 12/1992 | Clark et al. | 428/680 |
| 5,180,363 | 1/1993 | Idemoto et al. | 202/32 |
| 5,190,517 | 3/1993 | Zieve et al. | 604/22 |
| 5,231,086 | 7/1993 | Sollevi | 514/46 |
| 5,244,460 | 9/1993 | Unger et al. | 604/53 |
| 5,248,296 | 9/1993 | Alliger | 609/22 |
| 5,263,957 | 11/1993 | Davison | 606/169 |
| 5,269,309 | 12/1993 | Fort et al. | 128/661.01 |
| 5,322,055 | 6/1994 | Davison et al. | 601/2 |
| 5,324,299 | 6/1994 | Davison et al. | 606/167 |
| 5,342,292 | 8/1994 | Nita et al. | 604/22 |
| 5,344,420 | 9/1994 | Hilal et al. | 606/28 |
| 5,346,502 | 9/1994 | Estabrook et al. | 606/169 |
| 5,380,274 | 1/1995 | Nita | 604/22 |
| 5,380,316 | 1/1995 | Aita et al. | 606/7 |
| 5,382,162 | 1/1995 | Sharp | 433/116 |
| 5,389,096 | 2/1995 | Aita et al. | 606/15 |
| 5,425,704 | 6/1995 | Sakurai et al. | 604/22 |
| 5,438,554 | 8/1995 | Seyed-Bolorforosh et al. | 367/140 |
| 5,449,370 | 9/1995 | Vaitekunas | 606/169 |
| 5,452,733 | 9/1995 | Sterman et al. | 128/898 |
| 5,472,447 | 12/1995 | Abrams et al. | 606/169 |
| 5,501,228 | 3/1996 | LaFontaine et al. | 128/692 |
| 5,503,150 | 4/1996 | Evans | 128/653.1 |
| 5,507,738 | 4/1996 | Ciervo | 606/1 |
| 5,507,743 | 4/1996 | Edwards et al. | 606/41 |
| 5,509,916 | 4/1996 | Taylor | 606/13 |
| 5,526,815 | 6/1996 | Granz et al. | 128/660.03 |
| 5,540,656 | 7/1996 | Pflueger et al. | 604/22 |
| 5,542,917 | 8/1996 | Nita et al. | 604/22 |
| 5,546,947 | 8/1996 | Yagami et al. | 128/662.06 |
| 5,554,152 | 9/1996 | Aita et al. | 606/7 |
| 5,562,609 | 10/1996 | Brumbach | 604/22 |
| 5,562,610 | 10/1996 | Brumbach | 604/22 |
| 5,582,588 | 12/1996 | Sakurai et al. | 604/22 |
| 5,606,974 | 3/1997 | Castellano et al. | 128/662.06 |
| 5,628,743 | 5/1997 | Cimino | 606/1 |

OTHER PUBLICATIONS

Mirhoseini et al., "Myocardial Revascularization By Laser", Lasers in Surgery and Medicine, 3:241,245 (1983).

Mirhoseini et al., "Transventricular Revascularization By Laser", Lasers in Surgery and Medicine, 187–198 (1982).

Mirhoseini et al., "Revascularization Of the Heart By Laser", Journal of Micrsurgery, 253–260 (Jun. 1981).

"Laser Surgery Revascularizes the Heart in Treatment of Ischemic Heart Disease", Cover News, Chirurgia International.

"Punching Holes in the Heart With Lasers Can Stave Off Attacks When Arteries Clog", The Wall Street Journal, Medicine.

United States Catheter & Instrument Corporation Price List for Radiopaque Desilets–Hoffman Catheter Introducer.

Mirhoseini, "Laser Revascularization Of The Heart", New Frontiers In Laser Medicine and Surgery, 296–303.

Mirhoseini et al., "Lasers In Cardiothoracic Surgery", Chapter 21, pp. 216–232.

Cooper LaserSonics, Inc., Ultrasonic Surgucal Aspirator NS–100 Operator Manual, 1984, pp. 12, 13,16 ,17, and 29–33.

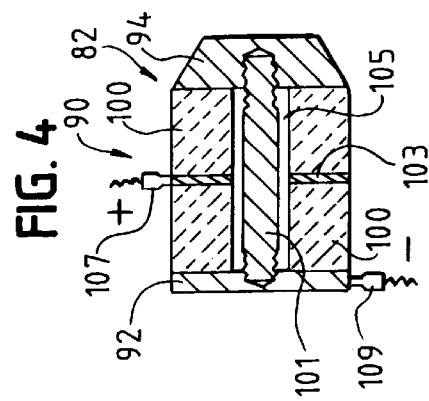
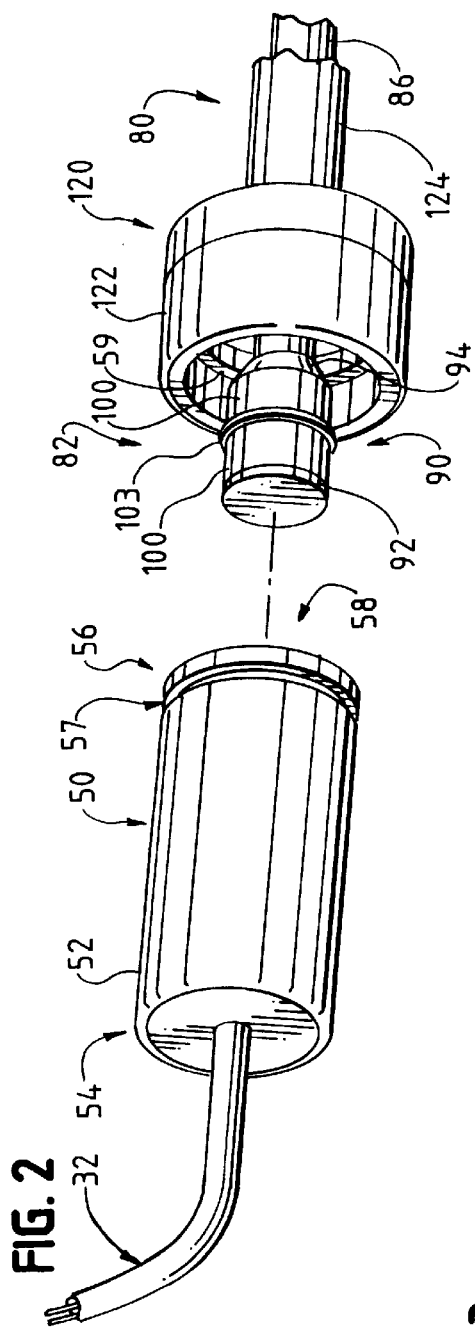
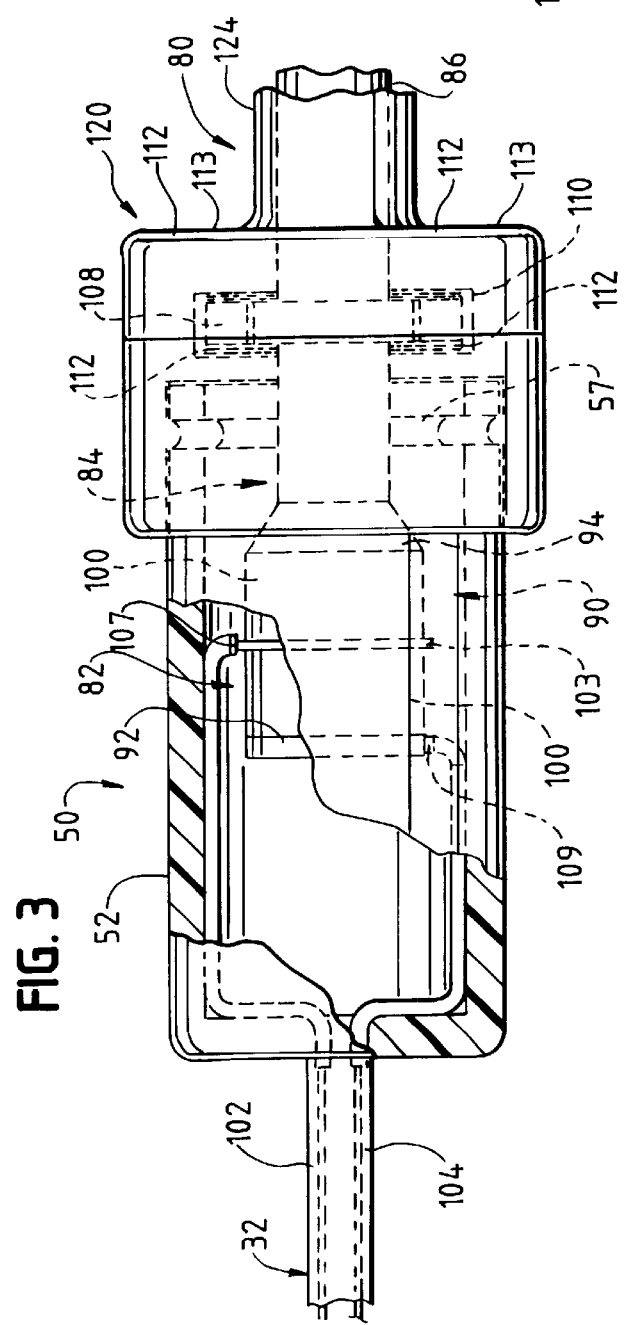

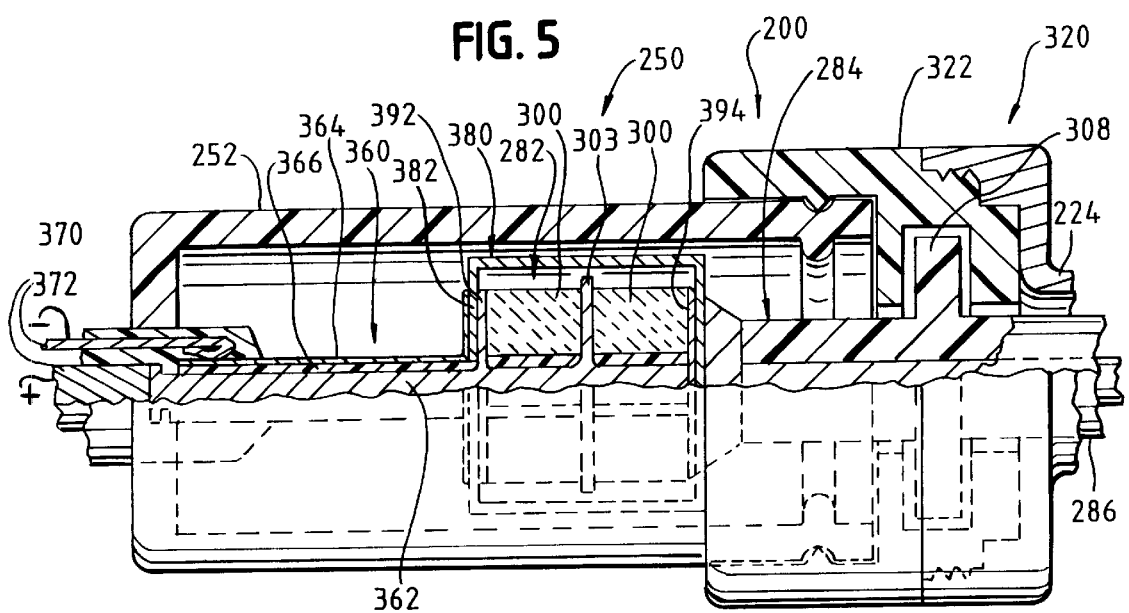
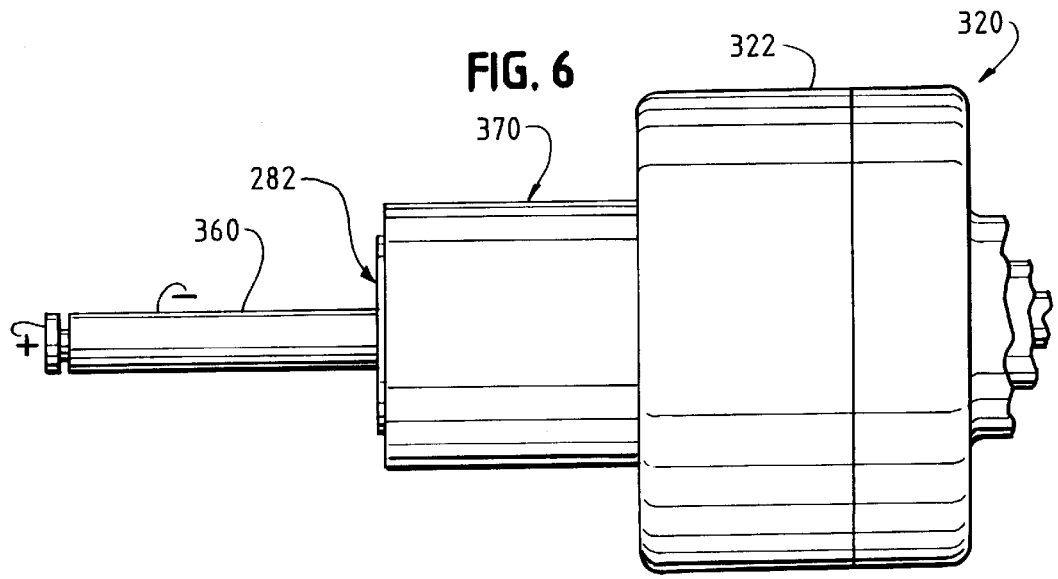

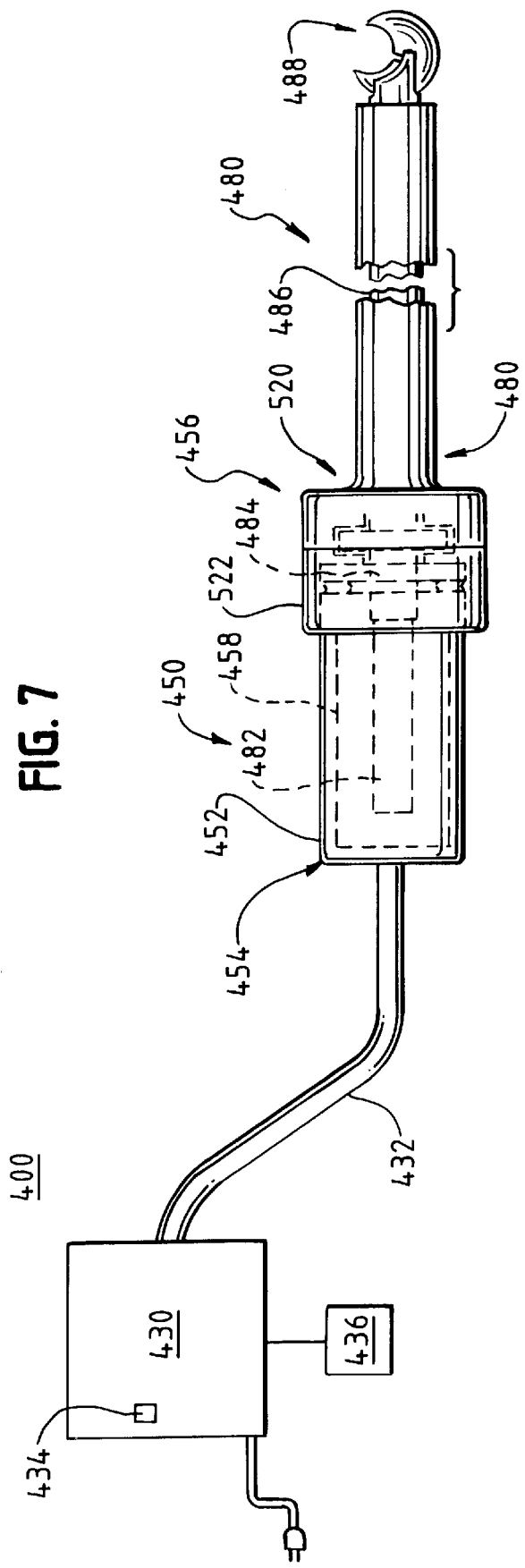

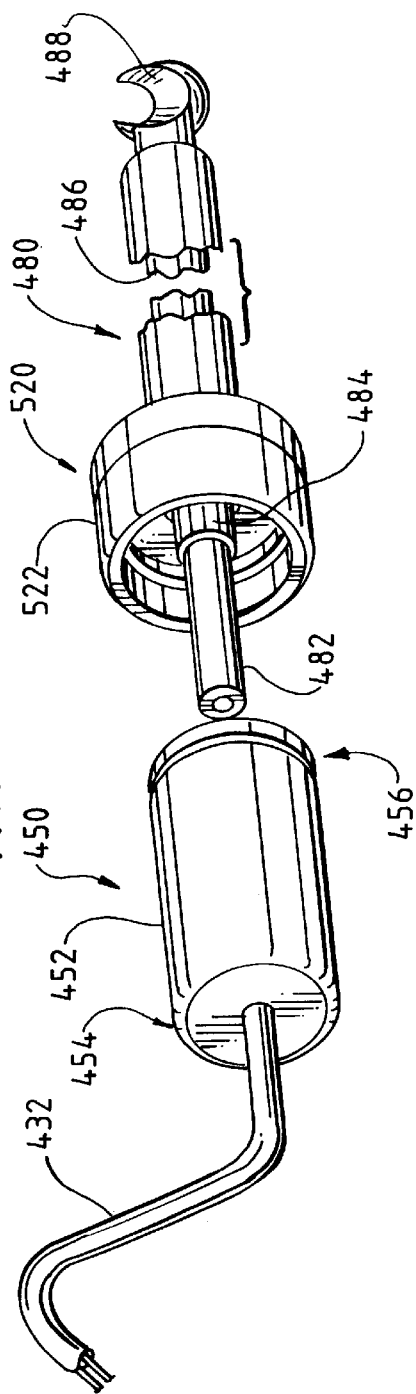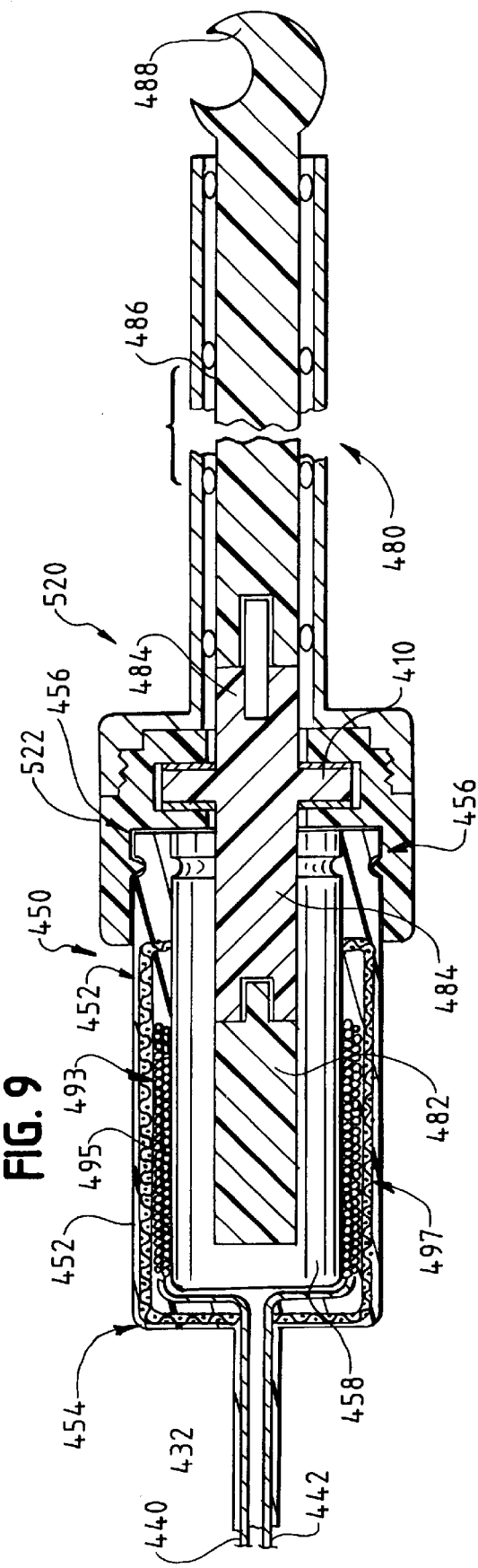
FIG. 8
FIG. 9

ULTRASONIC SURGICAL DEVICES

FIELD OF THE INVENTION

The present invention generally relates to surgical devices. More particularly, the present invention relates to ultrasonic surgical devices.

BACKGROUND OF THE INVENTION

Ultrasonic transmission devices are well known for use in a variety of applications, such as surgical operations and procedures. Ultrasonic surgical devices usually include a transducer assembly rigidly mounted within a handpiece assembly. The transducer assembly converts electrical energy into vibrational motion at ultrasonic frequencies. The vibrational motion is usually transmitted through a mounting device to vibrate a distal end of a transmission component, such as a working member. The working member is adapted to, for example, cut and coagulate tissue of a patient.

The working member is typically attached to the mounting device by a screw-type mechanism to form a junction. A separate torque wrench is usually used to tighten the working member onto the mounting device. However, it can be quite difficult to utilize a torque wrench to connect and disconnect the working member from the mounting device in a sterile field. Further, it can be cumbersome and time consuming to use a torque wrench to remove the working member during an operation or to tighten various working members to the mounting device. Additionally, the torque wrench can be mislaid or lost and may require calibration or replacement at frequent intervals to ensure accuracy.

When the working member is tightened on to the mounting device, the working member is usually mounted in a fixed position relative to the handpiece assembly. Thus, a user or surgeon may have to manipulate the handpiece assembly to properly align the working member with the desired tissue to be cut or penetrated. As a result, it may be difficult for the surgeon to manipulate the working member to a desired angular position relative to the tissue. Furthermore, conventional surgical devices also usually do not allow the transducer assembly to be readily changed, repaired, and/or replaced for various types of surgical operations.

SUMMARY OF THE INVENTION

In view of the above, the present invention relates to devices for facilitating attachment and detachment of an ultrasonic surgical instruments to a handpiece assembly. The surgical instruments can carry a transducer assembly and a working member. The working member of the surgical instruments can be rotated with respect to the handpiece assembly to allow the working member to positioned or aligned in a desired relationship with respect to the handpiece assembly and the tissue of a patient. The transducer assembly can also be rotated within the handpiece assembly. The transducer assembly and working member may also be removed from the surgical instruments for disposal or to permit resterilization so that they may be reused, refurbished, or recycled.

The surgical instruments of the present invention can be quickly coupled to and disengaged from the handpiece assembly without the use of a torque wrench. Other surgical instruments carrying a similar or different transducer assembly and/or working member can be easily and quickly attached to the handpiece assembly during a surgical operation. The surgical instruments may further be used on existing handpiece assemblies.

A surgical instrument in accordance with the present invention includes a transducer assembly adapted to vibrate at an ultrasonic frequency. An end effector is adapted to receive ultrasonic vibration from the transducer assembly and to propagate the ultrasonic vibration from a first end to a second end. The end effector is rotatable with respect to the handpiece assembly while the transducer assembly vibrates at the ultrasonic frequency.

A method in accordance with the present invention includes the steps of providing a handpiece assembly carrying an acoustic assembly having a transducer assembly and an end effector, and energizing the transducer to cause the end effector to vibrate. The method further includes the steps of rotating the end effector with respect to the handpiece assembly while the transducer is vibrating, and contacting the tissue of the patient with the end effector.

It is to be understood that both the foregoing general description and the following detailed description are exemplary and explanatory and are intended to provide further explanation of the invention as claimed.

The invention, together with attendant advantages, will best be understood by reference to the following detailed description of the preferred embodiments of the invention, taken in conjunction with the accompanying drawings.

BRIEF DESCRIPTION OF THE DRAWINGS

FIG. 2 is a partial exploded fragmentary view of the surgical system of FIG. 1;

FIG. 3 is a partial cut-away view and in partial cross-section of the surgical system of FIG. 1;

FIG. 4 is a cross-sectional view of a transducer assembly of the surgical system of FIG. 1;

FIG. 5 is a partial cut-away view and in partial cross-section of a surgical device of a surgical system;

FIG. 6 is a fragmentary side view of a surgical instrument of FIG. 5;

FIG. 7 is a side view of another surgical system;

FIG. 8 is an exploded fragmentary view of the surgical system assembly of FIG. 7; and FIG. 9 is a fragmentary cross-sectional view of the surgical system of FIG. 7.

DESCRIPTION OF THE PREFERRED EMBODIMENTS

Figure 1:
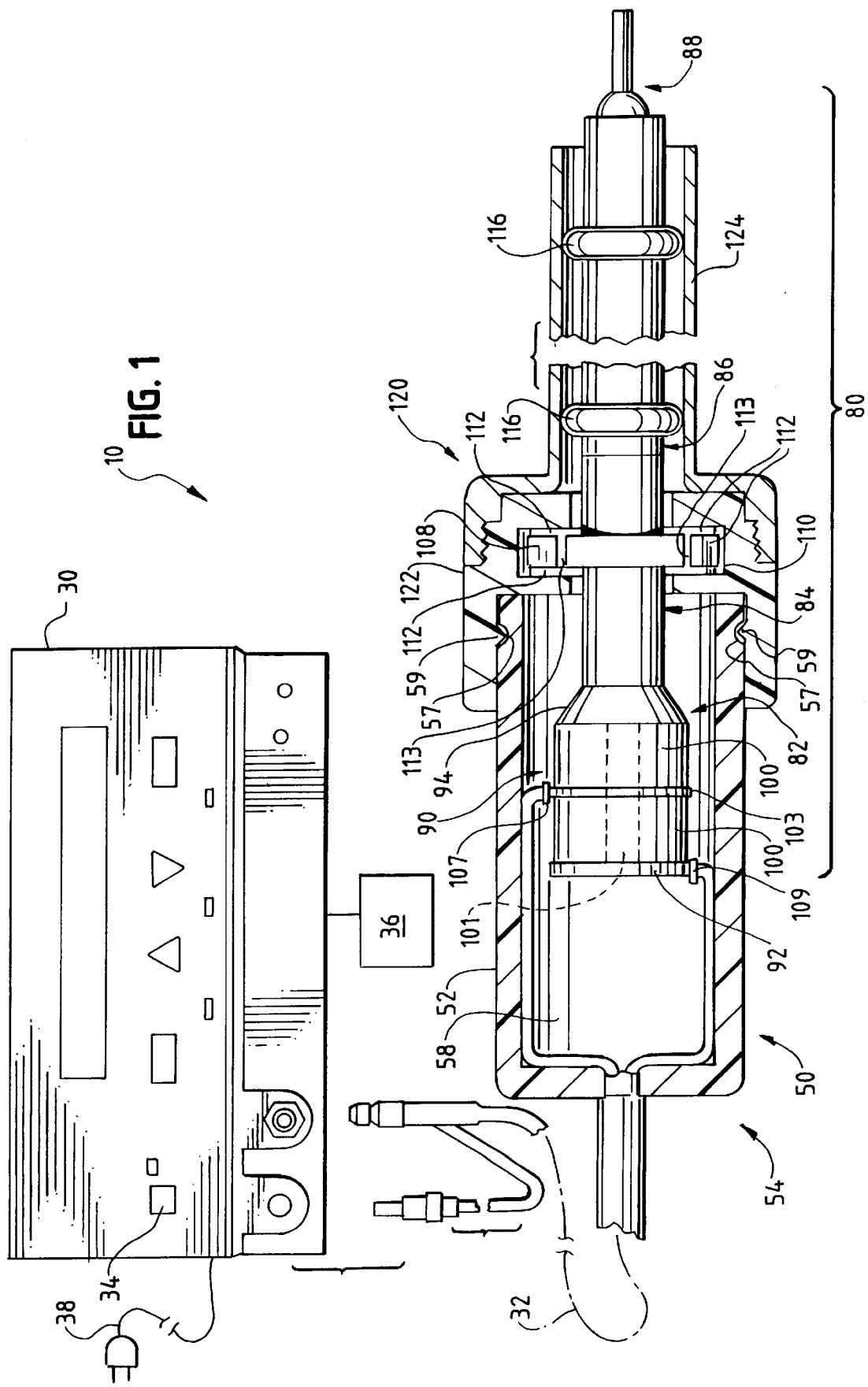
FIG. 1 is a partial cutaway view and in partial cross-section of a surgical system.

Before explaining the present embodiments in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Referring now to FIG. 1, a presently preferred embodiment of a surgical system 10 is illustrated. The surgical system 10 generally includes a generator 30, a handpiece assembly 50, and a surgical tool or instrument 120 carrying an acoustic or transmission assembly. The generator 30 sends an electrical signal through a cable 32 at a selected amplitude, frequency, and phase determined by a control system of the generator 30. As will be further described, the signal causes one or more piezoelectric elements of an acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude. An end effector 88 at the distal end of the acoustic assembly 80 is placed in contact with tissue of the patient to transfer the ultrasonic energy to the tissue. The cells of the tissue in contact with the end effector 88 of the acoustic assembly 80 will move with the end effector and vibrate.

As the end effector 88 couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the vibrational amplitude of the end effector 88, the amount of pressure applied by the user, and the sharpness of the end effector 88. The end effector 88 of the acoustic assembly 80 tends to focus the vibrational energy onto tissue in contact with the end effector 88, intensifying and localizing thermal and mechanical energy delivery.

As illustrated in FIG. 1, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector 88 at a predetermined vibrational amplitude level. The generator 30 may drive or excite the acoustic assembly 80 at any suitable resonant frequency of the acoustic assembly 80.

When the generator 30 is activated via the triggering mechanism 36, electrical energy is continuously applied by the generator 30 to a transducer assembly 82 of the acoustic assembly 80. A phase lock loop in the control system of the generator 30 monitors feedback from the acoustic assembly 80. The phase lock loop adjusts the frequency of the electrical energy sent by the generator 30 to match a preselected harmonic frequency of the acoustic assembly 80. In addition, a second feedback loop in the control system maintains the electrical current supplied to the acoustic assembly 80 at a preselected constant level in order to achieve substantially constant vibrational amplitude of the end effector 88. The electrical signal supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector 88 may be controlled by, for example, controlling the amplitude of the electrical signal applied to the transducer assembly 82 of the acoustic assembly 80 by the generator 30.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery. The generator 30 may be any suitable generator, such as Model No. GEN01, available from Ethicon Endo-Surgery, Inc.

Referring now to FIG. 2, the handpiece assembly 50 includes a housing or outer casing 52 adapted to isolate the operator from the vibrations of the acoustic assembly 80. The housing 52 is preferably cylindrically shaped and is adapted to be held by a user in a conventional manner, but may be any suitable shape and size. The housing 52 of the handpiece assembly 50 is preferably constructed from a durable plastic, such as Ultem®. It is also contemplated that the housing 52 may be made from a variety of materials including other plastics (i.e., liquid crystal polymer (LCP), nylon, or polycarbonate).

As shown in FIGS. 1–2, the handpiece assembly 50 generally includes a proximal end 54, a distal end 56, and centrally disposed axial opening or cavity 58 extending longitudinally therein. The distal end 56 of the handpiece assembly 50 is preferably adapted to be detachably coupled to the surgical instrument 120. The distal end 56 may have an annular groove 57 on its outer surface to engage and interlock with an annular flange of the surgical instrument 120. This arrangement allows the surgical instrument 120 to be detachably coupled to the housing 52 of the handpiece assembly 50. It will be recognized that the distal end 56 may have a plurality of annular grooves to allow the surgical instrument 120 to be attached at various positions along the distal end. Thus, the end effector can be positioned at various distances from the handpiece assembly 50. As those skilled in the art will recognize, the coupling and decoupling arrangement between the housing 50 of the handpiece assembly 52 and the surgical instrument 120 may be made by any suitable means without departing from the spirit and scope of the invention.

The proximal end 54 of the handpiece assembly 50 is coupled to the generator 30 by a cable 32. The cable 32 may include ducts or vents to allow air to be introduced into the handpiece assembly 50 to cool the transducer assembly of the acoustic assembly 80.

The surgical instrument 120 of the surgical system 10 generally includes a housing or adapter 122 carrying the acoustic assembly 80. The adapter 122 of the surgical instrument 120 is preferably the same general cross-sectional shape as the housing 52 of the handpiece assembly 50 (i.e., cylindrically shaped) and is adapted to fit over the distal end 56 of the handpiece assembly 50 as further shown in FIG. 3. The adapter 122 preferably includes an opening to allow the acoustic assembly 80 to extend therethrough and an annular flange 59 that is configured to fit within the groove 57 of the handpiece assembly 50. The adapter 122 may be fabricated from Ultem® or any suitable material and may be any size and shape which allows it to be coupled to the handpiece assembly 50.

The adapter 122 may also include a sheath 124 that has an opening extending longitudinally therethrough. The sheath 124 may be threaded onto the adapter 122 and configured to surround a portion of the acoustic assembly 80. Silicone rings 116 may be mounted around the acoustic assembly 80 to isolate the acoustic assembly 80 from the sheath 124. Alternatively, the acoustic assembly 80 may have polymeric material surrounding a portion of its outer surface to isolate the acoustic assembly 80 from outside contact.

Referring again to FIG. 1, the acoustic assembly 80 carried by the surgical instrument 120 generally includes a transducer stack or assembly 82, a mounting device 84, a working member or a transmission rod 86 and an end effector 88. The transducer assembly 82 and the transmission rod 86 may be integrally or permanently attached to the mounting device 84 or may be attached by any suitable means, such as, for example, an internal threaded connection. The transducer assembly 82, the mounting device 84, the transmission rod 86, and the end effector 88 may be acoustically tuned such that the length of each component is an integral number of one-half system wavelengths (n$\lambda$/2) where the system wavelength $\lambda$ is the wavelength of a preselected or operating longitudinal vibration frequency f of the acoustic assembly 80. It is also contemplated that the acoustic assembly 80 may be any suitable arrangement of acoustic elements. For example, the acoustic assembly 80 may comprise a transducer assembly and an end effector (i.e., the acoustic assembly 80 may be configured without a mounting device and a transmission rod).

As shown in FIG. 1, when the surgical instrument 120 is attached to the handpiece assembly 50, the transducer assembly 82 of the acoustic assembly 80 is adapted to be positioned in the opening 58 of the handpiece assembly 50. Once the surgical instrument 120 is attached to the handpiece assembly 50, the surgical instrument 120 may be rotated with respect to the handpiece assembly 50 to allow the acoustic assembly 80 to be turned or rotated. As such, the transducer assembly 82 can be rotated within the handpiece assembly 50 and the end effector 88 may also be rotated to a desired position. The surgical instrument 120 can be easily removed, and another surgical instrument (not shown) carrying an acoustic assembly can be quickly coupled to the handpiece assembly 50.

The transducer assembly 82 of the acoustic assembly 80 converts the electrical signal from the generator 30 into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength ($\lambda$/4).

As shown in FIG. 4, the transducer assembly 82 of the acoustic assembly 80 generally includes a transduction portion 90, end bells or cylinders 92 and 94, a connecting rod 101, a washer 103, and an insulating tube 105. The transducer assembly 82 may be an integral number of one-half system wavelengths (n$\lambda$/2) in length. It will be recognized that the transducer assembly 82 may be a "Langevin Stack" which includes a transduction portion sandwiched between two end bell or resonators. It is to be understood that the present invention may be alternatively configured to include a transducer assembly comprising a magnetostrictive transducer, electromagnetic transducer, piezoelectric transducer, electrostatic transducer, or any other suitable transducer.

The end bell 92 of the transducer assembly 82 is connected to the proximal end of the transduction section 90, and the end bell 94 is connected to the distal end of the transduction portion 90. The end bells 92 and 94 are connected together by the connection rod 101. The proximal and distal ends of the connection rod 101 are preferably threaded into cavities near the center of each of the end bells 92 and 94.

The end bells 92 and 94 may be fabricated from metal, aluminum, steel, titanium or any other suitable material. The end bells 92 and 94 have a length determined by a number of variables, including the thickness of the transduction section 90, the density and modulus of elasticity of material used in the end bells 92 and 94, and the fundamental frequency of the transducer assembly 82. The end bell 94 may be tapered inwardly from its proximal end to its distal end to amplify the ultrasonic vibration amplitude.

The washer 103 of the transducer assembly 82 is positioned between the two piezoelectric elements 100. The washer 103 may be fabricated from beryllium copper, aluminum, or any other suitable material. The washer 103 and the piezoelectric elements 100 are insulated from the connecting rod 101 by the insulating tube 105.

When the transducer assembly 82 is inserted into the handpiece assembly 50, the washer 103 is adapted to contact a positive conductor 107 and the end bell 92 is adapted to contact a negative conductor 109 as shown in FIGS. 1 and 3. The washer 103 and end bell 92 provide a slip ring electrical contact to maintain electrical contact with the conductors 107 and 109, respectively, while the transducer assembly 82 rotates within the handpiece assembly 82. The electrical conductors 107 and 109 may be biased inwardly by, for example, a spring, to remain in contact with the washer 103 and end bell 92, respectively. The electrical conductors 107 and 109 are electrically connected to wires 102 and 104, respectively, which are adapted to carry signals from the generator 30.

The transduction portion 90 of the transducer assembly 82 preferably comprises a piezoelectric section having piezoelectric elements 100. Preferably, the piezoelectric section includes two piezoelectric elements positioned between the two end bells 92 and 94. The piezoelectric elements 100 may be fabricated from any suitable material, such as, for example, lead-zirconate-titanate, lead meta-niobate, lead titanate, or other piezoelectric crystal material. It is contemplated that the piezoelectric section may include any suitable number piezoelectric elements.

The piezoelectric elements 100 are energized in response to the electrical signal supplied from the generator 30 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The mounting device 84 of the acoustic assembly 80 has a proximal end, a distal end, and may have a length substantially equal to an integral number of one-half system wavelengths. The proximal end of the mounting device 84 is preferably axially aligned and integrally coupled to the distal end of the transducer assembly 82 near an anti-node. (For purposes of this application, the term "near" is defined as "exactly at" or "in close proximity to.") It is also contemplated that the mounting device 84 may be attached to the transducer assembly 82 by any suitable means, and the mounting device 84 may be detachable from the transducer assembly 82.

As illustrated in FIGS. 1 and 3, the mounting device 84 is connected or mounted to the adapter 122 of the surgical instrument 120 near a node. The mounting device 84 may include an integral ring 108 that is configured to fit in an annular groove 110 formed in the adapter 122 of the surgical instrument 120 to couple the mounting device 84 to the adapter 122. A compliant member or material 112, such, for example, as a pair of silicone O-rings attached by stand-offs 113, may be placed between the annular groove 110 of the adapter 122 and the integral ring 108 of the mounting device 84 to reduce or prevent ultrasonic vibration from being transmitted from the mounting device 84 to the adapter 122.

The mounting device 84 may be configured to amplify the ultrasonic vibration amplitude that is transmitted through the acoustic assembly 80 to the distal end of the end effector 88. The mounting device 84 may, for example, comprise a solid, uniform or tapered horn. It is contemplated that the mounting device 84 may be any suitable shape, such as, for example, a stepped horn, a conical horn, an exponential horn, a unitary gain horn, or the like.

The distal end of the mounting device 84 is integrally coupled to the proximal end of the transmission rod 86. It is contemplated that the transmission rod 86 may be attached to the mounting device 84 by any suitable means, such as, for example, an internal threaded connection. The mounting device 84 may be coupled to the transmission rod 86 near an antinode.

The transmission rod 86 may have a length substantially equal to an integer number of one-half system wavelengths (n$\lambda$/2). The transmission rod 86 may be fabricated from a solid core shaft constructed out of material which propagates ultrasonic energy efficiently, such as, for example, a titanium alloy (i.e., Ti-6Al-4V) or an aluminum alloy. It is contemplated that the transmission rod 86 may be fabricated from any suitable material. The transmission rod 86 may amplify the mechanical vibrations transmitted through the transmission rod 86 to the end effector 88 as is well known in the art.

The distal end of the transmission rod 86 is integrally formed to the proximal end of the end effector 88 near an antinode. It is also contemplated that the end effector 88 may be detachable from the transmission rod 86. It will be recognized that the end effector 88 may be attached to the transmission rod 86 by any suitable means, such as, for example, an internal threaded connection.

The end effector 88 may have a distal region having a smaller cross-section area than a proximal region thereof, thereby forming a vibrational amplitude step-up junction. The step-up junction acts as a velocity transformer as known in the art, increasing the magnitude of the ultrasonic vibration transmitted from the proximal region to the distal region of the end effector 88.

The end effector 88 may have a length substantially equal to an integral multiple of one-half system wavelengths (n$\lambda$/2). The distal end of the end effector 88 is disposed near an antinode in order to produce the maximum longitudinal deflection at the distal end. When the transducer assembly 82 is energized, the distal end of the end effector 88 is configured to move longitudinally in the range of, for example, approximately 10 to 500 microns peak-to-peak, and preferably in the range of about 30 to 100 microns at a predetermined vibrational frequency, and most preferably at about 90 microns.

The end effector 88 may be made from a solid core shaft constructed of material which propagates ultrasonic energy, such as, for example, a titanium alloy (i.e., Ti-6Al-4V) or an aluminum alloy. It is contemplated the end effector 88 may be fabricated from any suitable material. It will also be recognized that the end effector 88 may have a surface treatment to improve the delivery of energy and desired tissue effect. For example, the end effector 88 may be micro-finished, coated, plated, etched, grit-blasted, roughened, or scored to enhance coagulation in tissue. Additionally, the end effector 88 may be sharpened or shaped to enhance its energy transmission characteristics. For example, the end effector 88 may be blade shaped, hook shaped, or ball shaped.

FIGS. 5–6 illustrate another preferred embodiment of a surgical device 200. The surgical device 200 includes a handpiece assembly 250 and a surgical instrument 320, which in many respects corresponds in construction and function to the previously described handpiece assembly 50 and surgical instrument 120 of the surgical system 10. Components of the handpiece assembly 250 and surgical instrument 320 which generally correspond to those components of the handpiece assembly 50 and surgical instrument 120 of the surgical system 10 are designated by like reference numerals in the two-hundred and three-hundred series.

The surgical instrument 320 preferably includes a coaxial plug 360 and an acoustically and electrically isolated barrier housing 380. The distal end of the coaxial plug 360 is attached to the proximal end of the transducer assembly 282. The distal end of the coaxial plug 360 is preferably connected to a receptacle or jack 370. The coaxial plug 380 includes a positive conductive shaft 362, a negative conductive sleeve or tube 364, and a non-conductive sleeve or tube 366. The conductive shaft 362 is preferably coupled to the washer 303, and the conductive sleeve 364 is coupled to the barrier housing 380. The receptacle 370 includes a positive conductor 372 and a negative conductor 372. The positive conductor 372 contacts the conductive shaft 362 and the negative conductor 372 contacts the conductive sleeve 364.

The barrier housing 380 of the surgical instrument 320 preferably comprises a tubular member 382 having an opening extending therethrough. The barrier housing 380 is preferably coupled to the end bells 392 and 394. The barrier housing 380 allows a negative charge to be applied to the end bells 392 and 394 and isolates the transducer assembly 282 from contact by a user when the surgical instrument 320 is removed from the handpiece assembly 250.

Referring now to FIGS. 7–9, another preferred embodiment of a surgical system 400 is illustrated. The surgical system 400 generally includes a generator 430, a handpiece assembly 450, and a surgical tool or instrument 520 carrying an acoustic or transmission assembly 480. The generator 430 sends an electrical signal through a cable 432 at a selected amplitude, frequency, and phase determined by a control system of the generator 430. The signal is provided to an energizing device 493 that generates a magnetic field that reacts with the acoustic assembly 480 to cause the assembly 480 to expand and contract. The expansion and contraction of the acoustic assembly 480 results in longitudinal waves of ultrasonic energy that propagate through the acoustic assembly 480 in an acoustic standing wave to vibrate the acoustic assembly 480 at a selected frequency and amplitude. An end effector 488 at the distal end of the acoustic assembly 480 is placed in contact with tissue of the patient to transfer the ultrasonic energy to the tissue as previously described.

The generator 430 includes a control system integral to the generator 430, a power switch 434, and a triggering mechanism 436. The generator 430 produces an electrical signal that is sent to the energizing device 493 as further described below, of the handpiece assembly 180.

The handpiece assembly 450 includes a housing or outer casing 452 adapted to isolate the operator from the vibrations of the acoustic assembly 480. The housing 452 is preferably cylindrically shaped and is adapted to be held by a user in a conventional manner, but may be any suitable shape and size. The housing 452 of the handpiece assembly 450 may be constructed from any suitable material as discussed above.

As illustrated in FIG. 9, the handpiece assembly 450 generally includes a proximal end 454, a distal end 456, an energizing device 493, a magnetic shield 497, and a centrally disposed axial opening or cavity 458 extending longitudinally therein. The distal end 456 of the handpiece assembly 450 is adapted to be detachably coupled to the surgical instrument 520 and the proximal end 454 is connected to a cable 432 as described above.

The energizing device 493 of the handpiece assembly 450 preferably comprises a coil 495 that is disposed around the outer circumference of the opening 458 of the handpiece assembly 450. The coil 495 may be embedded or sealed in insulating material, such as, for example, glass or plastic, to reduce the chance of steam degrading. The coil 495 is preferably electrically coupled to conductors 440 and 442 that transmit electrical signals from the generator 430 to energize the coil 495. The coil 495 generates a magnetic field that reacts with the transducer assembly 482. The transducer assembly 482 vibrates at an ultrasonic frequency in response to the magnetic field generated by the coil 495. The vibrations of the transducer assembly 482 are transmitted through the acoustic assembly 480 to vibrate the distal end of the end effector 488 at a desired frequency and amplitude as discussed above.

The magnetic shield 497 of the handpiece assembly 450 is preferably disposed around the coil 495 to reduce electromagnetic interference with other devices. The magnetic shield 497 preferably comprises copper mesh or foil. It will be recognized that the magnetic shield 497 may be fabricated from any suitable material.

The surgical instrument 520 of the surgical system 400 generally includes the a housing or adapter 522 carrying the acoustic assembly 480. The acoustic assembly 480 generally includes a transducer stack or assembly 482, a mounting device 484, a working member or a transmission rod 486 and an end effector 488. The acoustic assembly 480 is substantially similar to the acoustic assembly described above except that the transducer assembly 482 is preferably a magnetostrictive transducer and the end effector 488 is configured as a hook-like member. It is contemplated that the end effector 488 may be any suitable shape, and the transducer 482 may be any suitable transducer.

The transducer assembly 482 of the acoustic assembly 480 is preferably energized by the magnetic field established by the coil 495 of the handpiece assembly 450. The transducer assembly 482 preferably includes a stack of magnetostrictive material, such as, for example, Terfenol™ or other suitable material. It is contemplated that the transducer assembly 484 may include a permanent magnet that may move longitudinally within the handpiece assembly 480. This arrangement can allow the transducer assembly 482 to be positioned in a relatively small opening or cavity (i.e. 0.5" diameter or less).

When the surgical instrument 520 is attached to the handpiece assembly 450, the transducer assembly 482 is positioned within the opening 458 of the handpiece assembly 450. The surgical instrument 520 can be rotated with respect to the handpiece assembly 450 to allow the acoustic assembly 480 to be turned or rotated. As such, the transducer assembly 482 can rotate within the opening 458 of the handpiece assembly 450 and the end effector 488 may also be rotated to a desired position. The surgical instrument 520 may also be coupled to various positions on the distal end of the handpiece assembly 450 to adjust the distance of the distal end of the end effector with respect to the handpiece assembly 450.

A displacement sensor (not shown), such as, for example, a capacitance sensor or laser interferometer, may be used to detect the displacement of the transducer assembly 482. The sensor may provide feedback signals indicative displacement of the transducer assembly 482. This feedback signal may be provided to the generator in order to control or to vary the electric signals produced by the generator. It is contemplated that the sensor may detect the displacement of any part of the acoustic assembly and may be incorporated into any of the embodiments disclosed herein.

The use of the surgical systems will now be described in reference to FIGS. 1–4. Initially, a surgeon connects the handpiece assembly 50 to the generator 30 and attaches the surgical instrument 120 to the handpiece assembly 50. The surgical instrument 120 can be attached to the handpiece assembly without the use of any tools (i.e., a torque wrench). The surgeon can also adjust the distance of the end effector from the handpiece assembly 50 by sliding the adapter 122 inwardly or outward on the distal end of the handpiece assembly.

While holding the handpiece assembly 50 with one hand, the surgeon can move the handpiece assembly 50 to the surgical site. The surgeon then activates the generator 30 to cause the end effector 88 to vibrate. The end effector 88 can then be inserted into an incision or port in the body of a patient.

While holding the handpiece assembly 50 with one hand, the surgeon can rotate the surgical instrument 120 to cause the end effector 88 to rotate to a selected position with respect to the handpiece assembly 50. When the surgical instrument 120 is rotated, the transducer assembly 82 (which may be vibrating) is also rotated within the handpiece assembly 50. The surgeon then may contact the tissue with the end effector 88 to apply the ultrasonic energy thereto. After applying the ultrasonic energy to the tissue, the surgeon may rotate the surgical instrument and/or adjust the distance of the end effector 88 from the handpiece assembly 50.

Once the surgeon has finished using the surgical instrument 120, the surgeon may deactivate the generator 30 and remove the surgical instrument with one hand while holding the handpiece assembly 50 in the other hand. After the surgical instrument 120 has been removed from the handpiece assembly 50, the surgeon may attach a new or different surgical instrument with one hand while holding the handpiece assembly 50 in the other hand. The process may then be continued with the new surgical instrument.

The surgical instruments of the present invention can be easily attached or removed from a handpiece assembly. The surgical instruments can carry a transducer assemble and an end effector. The surgical instruments can rotate with respect to the handpiece assembly without twisting the cable attached to the handpiece assembly. As a result, the transducer assembly and end effector can also be rotated with respect to the handpiece assembly.

The surgical instruments may be pre-assembled before an operation so that a user may attach various surgical instruments onto the handpiece assembly without using any torque tightening tools, such as a torque wrench, during surgery. The components of the surgical instruments can be removed from the handpiece for sterilization and for reuse, or the components may be disposed of or replaced with other components.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. An ultrasonic surgical instrument for use with a handpiece assembly comprising:
    a transducer assembly adapted to vibrate at an ultrasonic frequency, the transducer assembly rotatable with respect to the handpiece assembly while vibrating at the ultrasonic frequency;
    a mounting device having a first end and a second end, the mounting device adapted to receive ultrasonic vibration from the transducer assembly and to propagate the ultrasonic vibration from the first end to the second end of the mounting device, the first end of the mounting device being coupled to the transducer assembly the mounting device being adapted to rotate on one end of the handpiece assembly;
    a transmission rod having a first end and a second end, the transmission rod adapted to receive ultrasonic vibration from the transducer assembly and to propagate the ultrasonic vibration from the first end to the second end of the transmission rod, the first end of the transmission rod being coupled to the second end of the mounting device; and
    an end effector having a first end and a second end, the end effector adapted to receive the ultrasonic vibration from the transmission rod and propagate the ultrasonic vibration from the first end to the second end of the end effector, the first end of the end effector coupled to the second end of the transmission rod.

2. The surgical instrument of claim 1 wherein the end effector is rotatable at the same rate as the transducer assembly when the transducer is rotated.

3. The device of claim 1 wherein the collar member includes a detachable mount to allow the transducer assembly be be removed from the handpiece assembly during a surgical operation.

4. A surgical instrument for use with a handpiece assembly comprising:
    a transducer assembly adapted to vibrate at an ultrasonic frequency;
    a transmission rod having a first end and a second end, the transmission rod adapted to receive ultrasonic vibration from the transducer assembly and to propagate the ultrasonic vibration from the first end to the second end, the first end of the transmission rod coupled to the transducer assembly; and
    an end effector having a first end and a second end, the end effector adapted to receive ultrasonic vibration from the transmission rod and to propagate the ultrasonic vibration from the first end to the second end, the first end of the end effector being coupled to the second end of the transmission rod, the end effector being rotatable with respect to the handpiece assembly while the transducer assembly vibrates at the ultrasonic frequency.

5. The surgical instrument of claim 4 wherein the transducer assembly includes one of a magnetostrictive transducer, an electromagnetic transducer, an electrostatic transducer, a piezoelectric transducer, and a magnet.

6. The surgical instrument of claim 4 further comprising an energizing device to generate an electric field to excite the transducer assembly.

7. The surgical instrument of claim 6 wherein the energizing device comprises a coil.

8. The surgical instrument of claim 4 wherein the transducer assembly is rotatable with respect to the handpiece assembly while the transducer assembly is vibrating at the ultrasonic frequency.

9. The surgical instrument of claim 4 further including a coaxial plug mounted to the transducer assembly.

10. The surgical instrument of claim 4 wherein the surgical instrument can be attached to the handpiece assembly without the use of a torque limiting device.

11. The surgical instrument of claim 4 further comprising a generator coupled to the handpiece assembly.

12. The surgical instrument of claim 4 wherein the transducer assembly includes at least one piezoelectric element disposed between a first and second end bell.

13. The surgical instrument of claim 12 further comprising a washer disposed between the first and second end bells.

14. The surgical instrument of claim 12 further comprising a connecting rod coupled between the end bells.

15. The surgical instrument of claim 4 wherein the transmission rod is permanently attached to the transducer assembly.

16. The surgical instrument of claim 4 further comprising a sensor responsive to the displacement of one of the transducer assembly, the transmission rod, and the end effector.

17. The surgical instrument of claim 4 further comprising a mounted device coupled between the transmission rod and the transducer assembly.

18. A surgical instrument for use with a handpiece assembly comprising:
    a transducer assembly adapted to vibrate at an ultrasonic frequency;
    an end effector having a first end and a second end, the end effector adapted to receive ultrasonic vibration from the transducer assembly and to propagate the ultrasonic vibration from the first end to the second end, the end effector being rotatable with respect to the handpiece assembly while the transducer assembly vibrates at the ultrasonic frequency.

19. A method of applying ultrasonic energy to tissue of a patient comprising the steps of:
    providing a handpiece assembly carrying an acoustic assembly, the acoustic assembly having a transducer assembly and an end effector;

energizing the transducer to cause the end effector to vibrate;

rotating the end effector with respect to the handpiece assembly while the transducer assembly is vibrating; and contacting the tissue of the patient with the end effector.

20. The method of claim 19 further comprising the step of:

rotating the transducer assembly with the transducer is energized.

21. The method of claim 19 further comprising the step of:

detaching the acoustic assembly by a surgeon with one hand while holding the handpiece assembly with the other hand during an operation.

22. The method of claim 20 further comprising the step of:

attaching a different acoustic assembly by a surgeon with the one hand while still holding the handpiece assembly with the other hand.

23. The method of claim 19 further comprising the step of:

adjusting the distance of the distal end of the end effector from the distal end of the handpiece assembly.

24. An ultrasonic surgical instrument for use with a handpiece assembly, comprising a transducer assembly adapted to rotate at an ultrasonic frequency, the transducer assembly rotatable with respect to the handpiece assembly while vibrating at the ultrasonic frequency;

a mounting device having a first end and a second end, the mounting device adapted to receive ultrasonic vibration from the transducer assembly and to propagate the ultrasonic vibration from the transducer assembly and to propagate the ultrasonic vibration from the first end to the second end of the mounting device, the first end of the mounting device coupled to the transducer assembly and rotatable on one end of the handpiece assembly; and an end effector having a first end and a second end, the end effector adapted to receive ultrasonic vibration propagated by the mounting device and to propagate the ultrasonic vibration from the first end to the second end effector.

25. The surgical instrument of claim 24 further comprising a transmission rod coupling the end effector to the mounting device, the transmission rod adapted to propagate ultrasonic vibration from the second end of the mounting device to the first end of the end effector.

\* \* \* \* \*